United States Patent [19]

Hewson et al.

[11] Patent Number: 5,556,425

[45] Date of Patent: Sep. 17, 1996

[54] ESOPHAGEAL/STOMACH PLACEMENT ELECTRODE

[75] Inventors: Roy Hewson, Tamworth, N.H.; J. Richard Hewson, Plymouth; Carl E. Hewson, Yarmouth, both of Mass.

[73] Assignee: Brunswick Biomedical Technologies, Inc.

[21] Appl. No.: 345,529

[22] Filed: Nov. 28, 1994

[51] Int. Cl.$^6$ ........................................... A61N 1/05
[52] U.S. Cl. .................... 607/124; 604/282; 128/642
[58] Field of Search ........................ 607/116, 122, 607/124–126, 133, 656–658; 128/642; 604/281, 282; 600/139, 146, 149, 150; 606/47

[56] References Cited

U.S. PATENT DOCUMENTS

| | | | |
|---|---|---|---|
| 3,890,977 | 6/1975 | Wilson | 604/281 |
| 4,706,688 | 11/1987 | Don Michael | 128/642 |
| 5,170,803 | 12/1992 | Hewson et al. | 607/124 |
| 5,197,491 | 3/1993 | Anderson et al. | 607/133 |
| 5,222,949 | 6/1993 | Kaldany | 128/656 X |
| 5,345,937 | 9/1994 | Middleman et al. | 128/772 X |
| 5,364,352 | 11/1994 | Cimino et al. | 604/95 |

*Primary Examiner*—William E. Kamm
*Assistant Examiner*—Jeffrey R. Jastrzab
*Attorney, Agent, or Firm*—Wolf, Greenfield & Sacks, P.C.

[57] ABSTRACT

An esophageal/stomach placement electrode comprises a flexible tubular member designed to be inserted into the esophagus and/or stomach. An electrode is carried by the tube in the region of its distal end. The tube is hinged by its distal end which enables the end of the tube to laterally actuate in the esophagus or the stomach. An actuating mechanism is disposed in the tube in the region of the hinge and is controlled from a point external to the body for causing the distal end of the tube to actuate laterally, and engage the esophagus or stomach with it. The inner portion of the hinge is more bendable than the outer portion. Additionally, the control cables are all within the tubular member.

14 Claims, 6 Drawing Sheets

ESOPHAGEAL/STOMACH PLACEMENT ELECTRODE

FIELD OF THE INVENTION

This invention relates to esophageal/stomach electrodes and more particularly an electrode that may be inserted down a patient's esophagus and enter the stomach with a portion of the electrode in contact with the stomach wall in a position favorable for electrically stimulating the ventricle of the heart in cooperation with an external electrode placed on the patient's chest.

This invention permits ventricular pacing with a current of 5 to 50 milliampers. This low current pacing is well tolerated by the patient as it is pain free.

There are a number of medical procedures in which esophageal electrodes are used for various purposes. Examples include defibrillating and pacing the heart as well as stimulating breathing. Examples of the use of esophageal electrodes in such procedures are shown in several U.S. Pat. Nos., including 4,574,807; 4,683,890; 4,735,206; and 4,960,133. An esophageal electrode may be used as an ECG pickup. Those patents are herein incorporated by reference. Many of these procedures may be substantially enhanced and facilitated if the electrode is capable of being moved close to the organ of the body being treated, such as the ventricles of the heart.

Frequently, patient care in a hospital and emergency care outside the hospital require ventricular pacing. Customarily, this is an invasive procedure and must therefore be performed in a sterile atmosphere and the procedure requires a considerable period of time to perform. Many of the patents identified above disclose a method and apparatus employing an internal, non-invasive esophageal electrode in combination with an external chest electrode, which are much more convenient to use, more efficient in performing the intended function, and do not require the presence of a physician.

The techniques described in the above-identified patents relating to pacing and/or defibrillation may be made more efficient if the electrode is positioned as close to the ventricle of the heart as possible. The closer the electrode is to the ventricle, the less electrical energy is needed to perform the pacing or defibrillating functions and the more confident the attendant may be that the current flow between the internal and the external electrodes is along the desired path.

There have been many attempts to improve on the esophageal electrode devices of the prior art. Two examples of such devices are U.S. Pat. Nos. 5,170,803 issued Dec. 15, 1992, and 5,197,491, issued Mar. 30, 1993. Each reference is incorporated herein by reference. Pat. No. 5,170,803 teaches an esophageal displacement electrode having a flexible tube member which is designed to be inserted into the esophagus. The tube is hinged near the distal end which enables the end of the tube to displace laterally in the esophagus. The actuation mechanism is disposed in the tube in the region of the hinge and is controlled from a point external of the body. The mechanism for deflecting the distal end of the tube includes a rigid pin having two chords one connected to each end. The rigid pin is aligned generally parallel to the axis of the tube and positioned at the distal portion of the tube in the vicinity of the hinge. A first cord is attached to the proximal end of the pin and extends out the proximal end of the tube. The other cord is attached to the distal end of the pin and extends through a port located distally of the hinge in the tube and reenters in the tube through a second port proximal of the hinge and then extends out the proximal end of the tube. By pulling on the cord attached to the distal end of the pin, the pin may be positioned adjacent to the distal port and continued pulling of the cord will cause the tube to bend at the hinge.

Pat. No. 5,197,491 teaches a similar device adapted for use in both the esophagus and the stomach. More specifically, the tube may be extended through the esophagus into the stomach where the distal end of the tube can be bent in the manner just described so that the electrode may be placed in a more proximal location to the heart.

The present invention optimizes the devices of the '803 and '481 patents. More specifically, the present invention is directed to an esophageal/stomach placement electrode to achieve greater efficiency in the practice of placing an electrode near the heart for pacing and to overcome the technical limitations contained in the prior art. One object of the present invention is to provide a tube without holes in the lateral exterior surface and which will angularly displace in the esophagus and stomach. Another object of the present invention is to eliminate the possibility of any abrasion which may be caused by the exposed controlling cable when the end of the tube is displaced angularly.

To accomplish these objectives, the present invention provides a tube in which the controlling cable is entirely within the tube. An electrode tip is disposed at the distal end of the tube and a control device is at the proximal end. At the bendable portion, one side of the tubing has been cut away and remolded with softer material. This facilitates the bending of the tube during the operation of the device. A tip wire is attached to the tip of the tube and a rigidizing member is placed at the bendable portion of the tube to make the tube rigid for insertion into the esophagus and the stomach. The tip wire, which is attached to the electrode tip, is operatively connected with the rigidizing member. A second wire is attached to the proximal end of the rigidizing member and extends out the proximal end of the tube. A sleeve is crimped to the tip wire at its proximal end and is located within the rigidizing member. The distal end of the rigidizing member is spun to a smaller diameter such that the tip wire may pass through freely and the sleeve will not pass through.

In operation, the actuator wire is pulled causing the rigidizing member to retract toward the proximal end of the tube. The rigidizing member retracts away from the bendable portion of the tube and once retracted away from the bendable portion of the tube pulls the tip wire to effect an angular displacement of the distal end. A spring may be provided to bias the rigidizing member toward the distal end of the tube. The spring causes the rigidizing member to move toward the bendable portion and straighten the tube when the actuation wire is released. This causes the tube to be straight in its normal position and provides for an easier entrance into and withdrawal from the esophagus.

In accordance with the present invention, once the tube is inserted, the last couple of inches of the tube is bent to move the electrode to a location proximal to the heart. Greater efficiency in the performance of the procedures is effected because the electrode is positioned closer to the heart, and as a result, less electrical power is needed for the electrode placement device to perform its desired function. This invention permits ventricular pacing with a current of 5 to 50 milliampers. This low current pacing is well tolerated by the patient as it is pain free.

This invention will be better understood and appreciated from the following detailed description of the preferred embodiment thereof, selected for purposes of illustration and shown in the accompanying drawings.

DETAILED DESCRIPTION OF THE INVENTION

Figure 1:
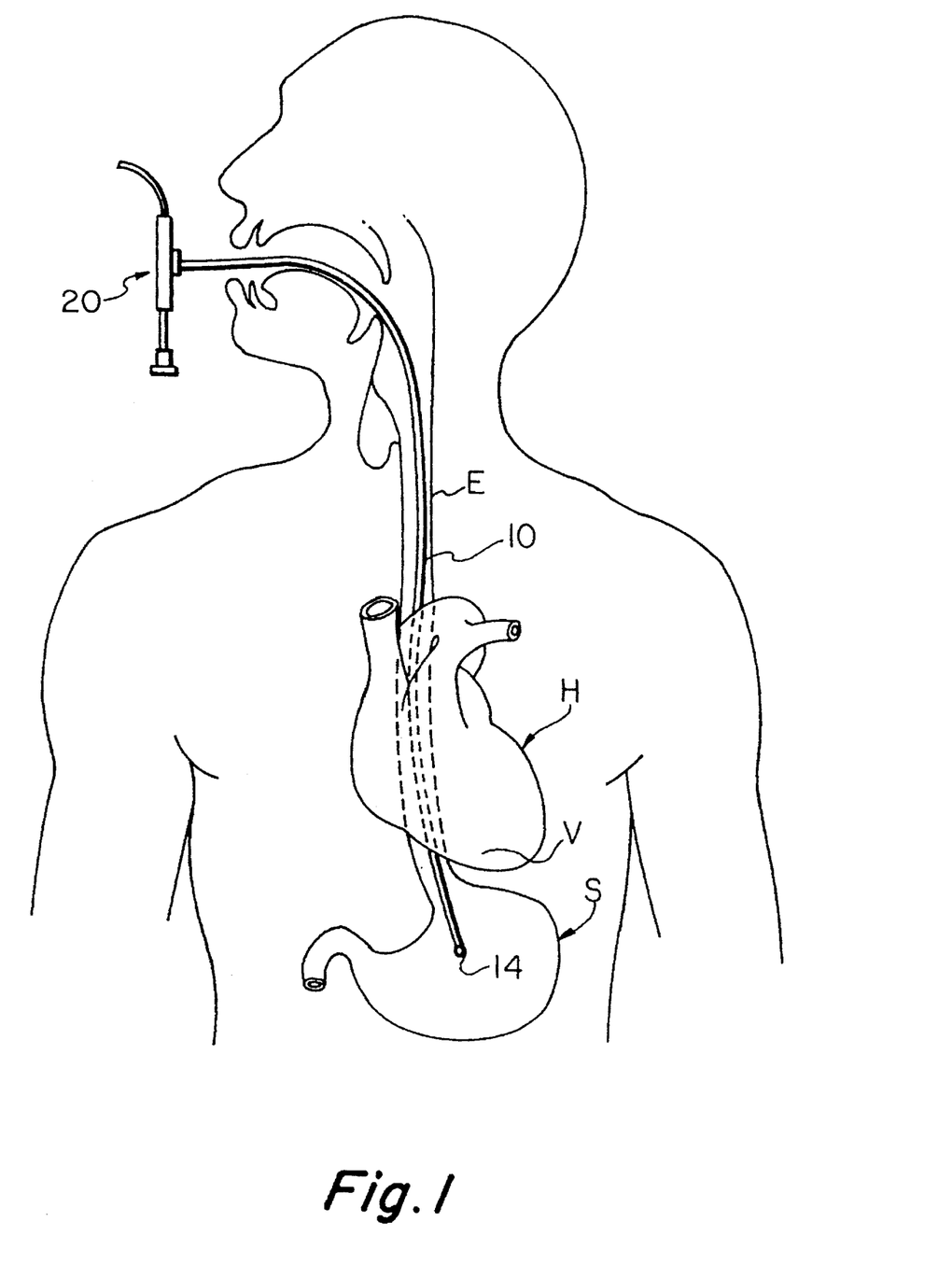
FIG. 1 is a diagrammatic front view of a patient suggesting the heart and esophagus and showing without details the esophageal placement electrode of the present invention disposed in the esophagus.
Figure 4:
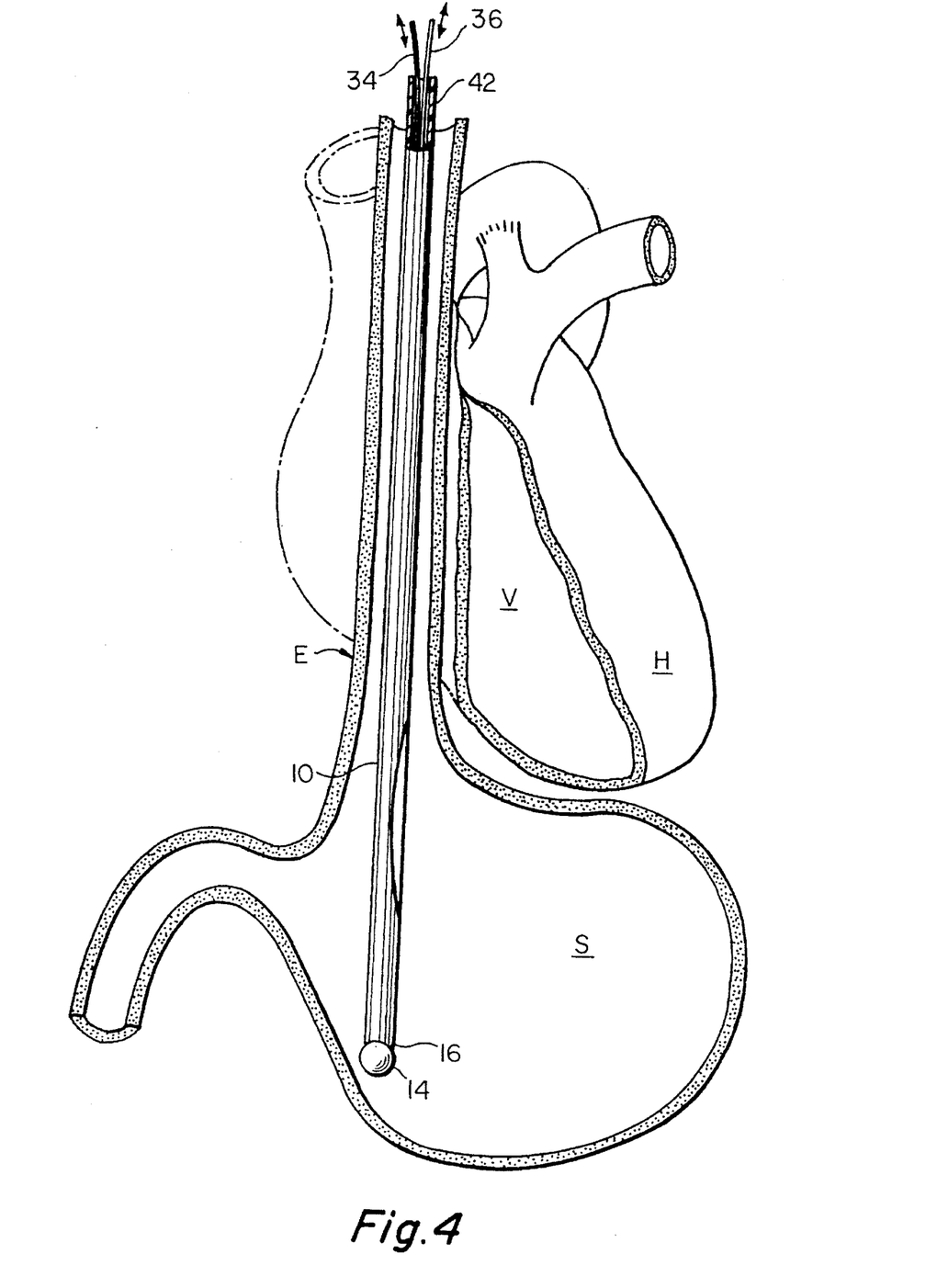
FIG. 4 is an enlarged cross-sectional view of esophageal/stomach placement electrode in the esophagus and with the distal end thereof in the rigidized position.
Figure 5:
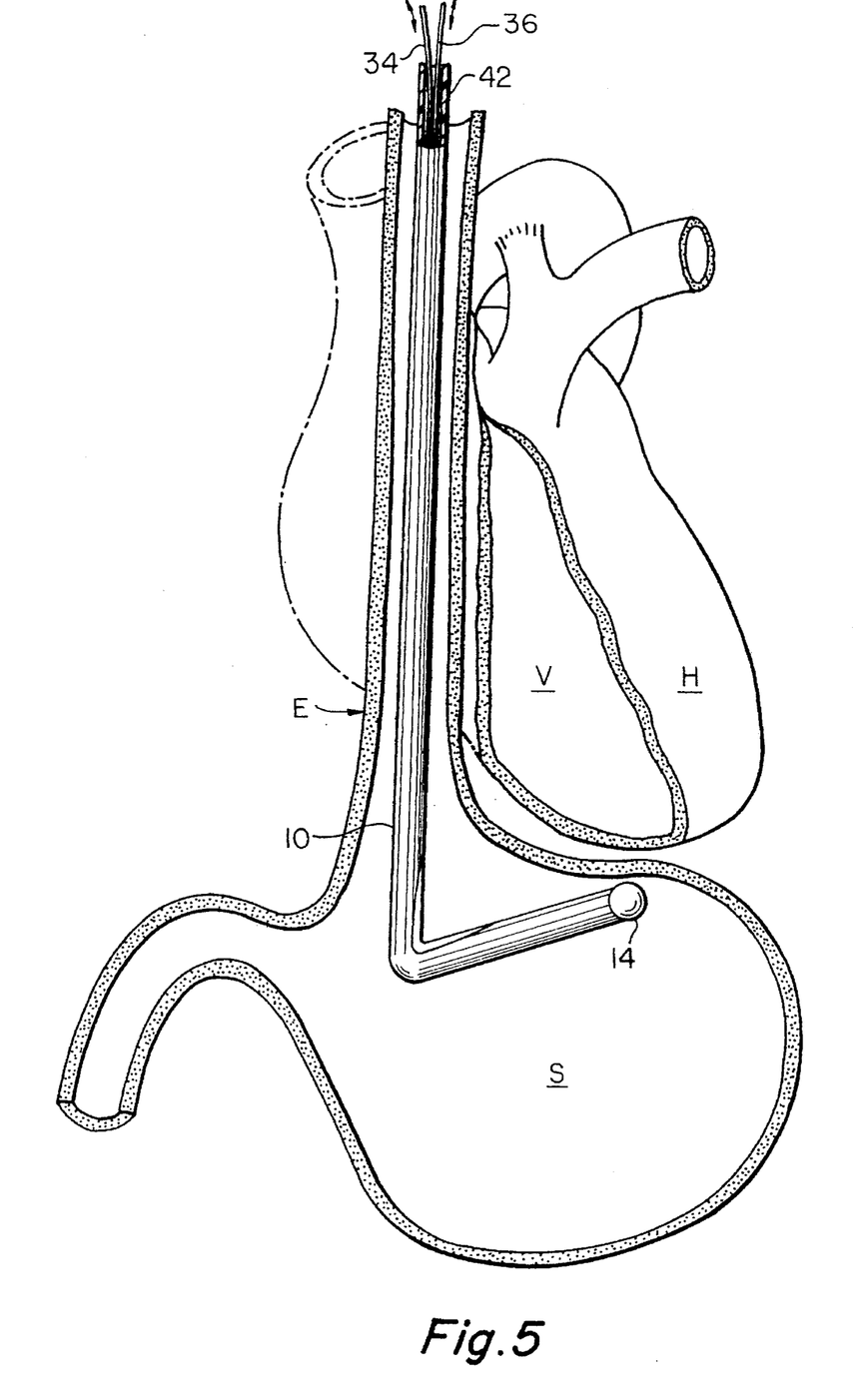
FIG. 5 is a view similar to FIG. 4 showing the electrode in its actuated position.
Figure 6:
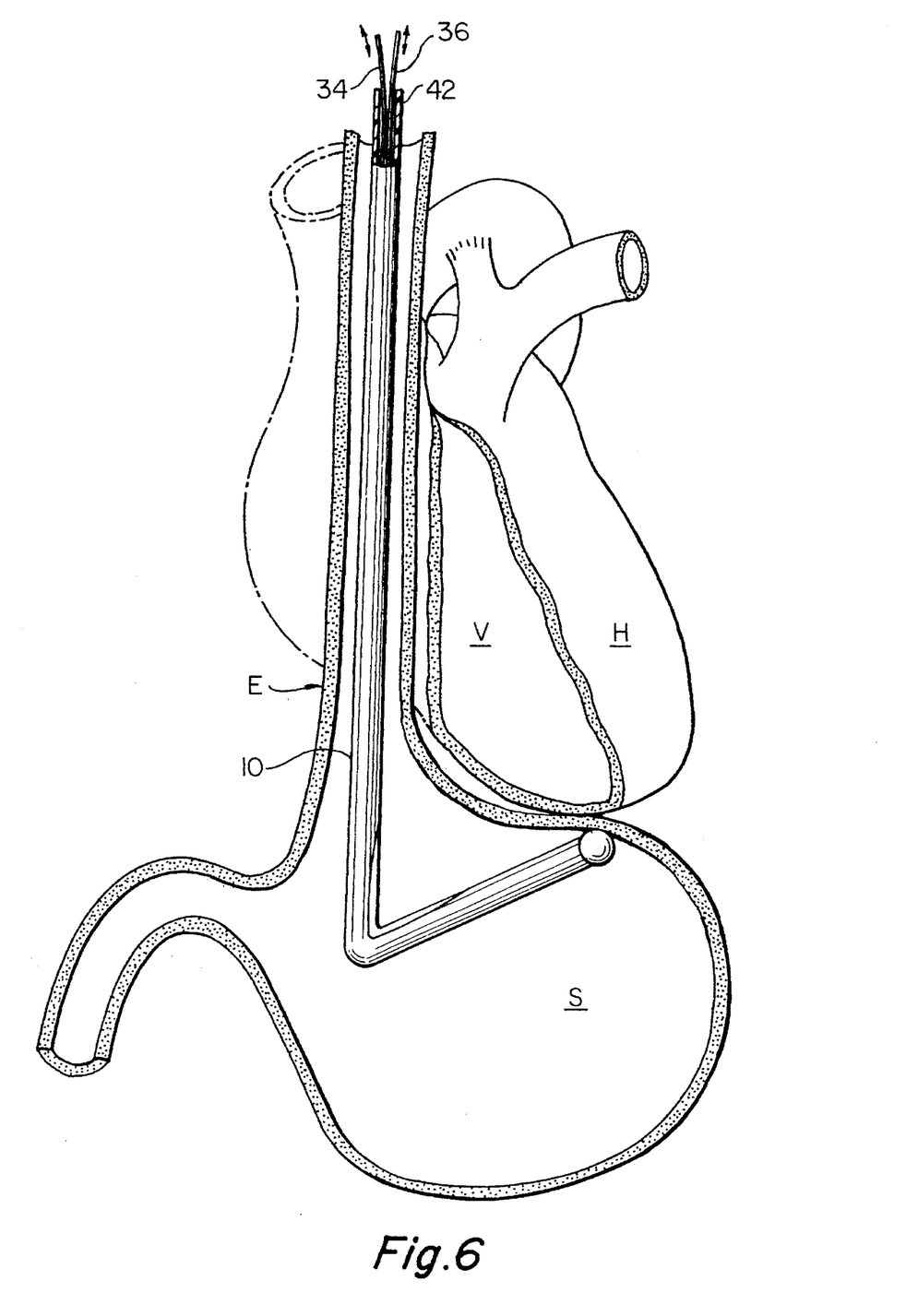
FIG. 6 shows the esophageal/stomach placement electrode in its fully actuated position and at a position proximate to the heart.

In FIG. 1 the torso and head of a patient are shown along with the patient's heart H and esophagus E. The esophagus is located posterior and spaced from the ventricle V of the heart H. The esophageal/stomach placement electrode shown extends through the patient's mouth and esophagus into the stomach with its distal end located close to the ventricle V. Alternately, the electrode may be placed in the lower third of the esophagus. The present invention enables the distal end of the esophageal/stomach placement electrode to angularly displace within the esophagus or the stomach and thereby place the esophageal/stomach placement electrode in closer proximity to the heart. The use of the esophageal/stomach placement electrode is illustrated in FIGS. 4–6, and is described infra.

Figure 2A:
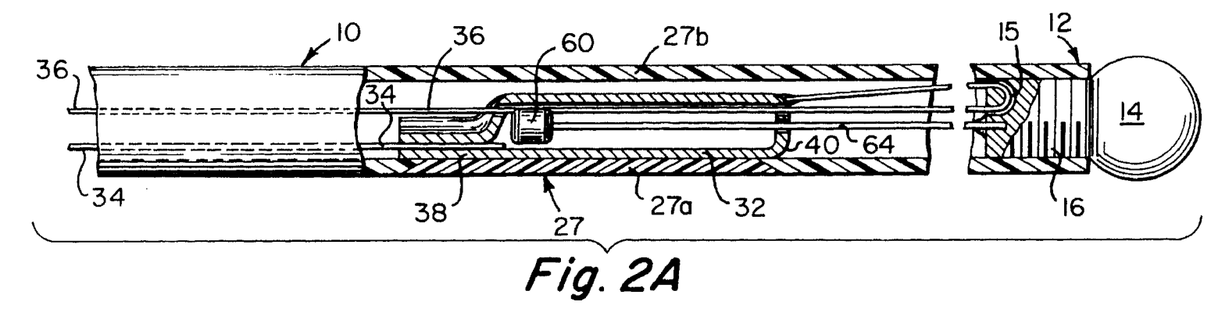
FIG. 2A shows a preferred embodiment of the esophagael-stomach placement electrode.
Figure 2B:
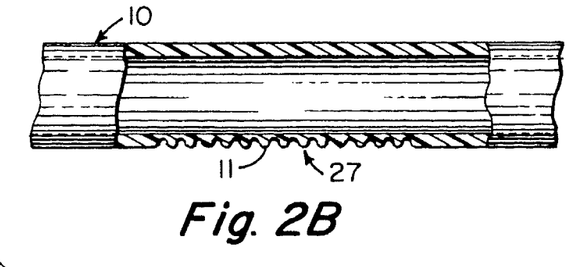
FIG. 2B an alternate design of the invention having a corrugated bendable portion.
Figure 2C:
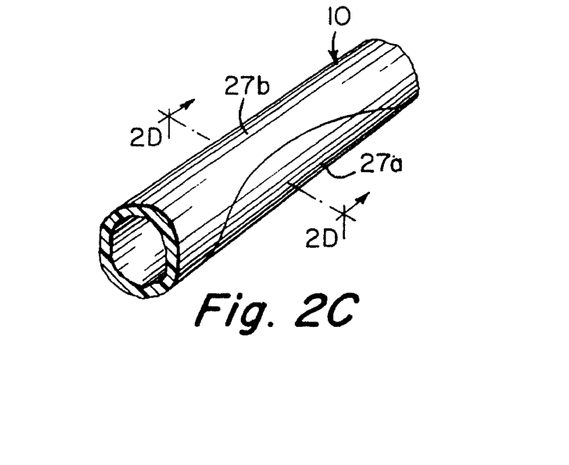
FIG. 2C shows the two materials of the bendable portion.
Figure 2D:
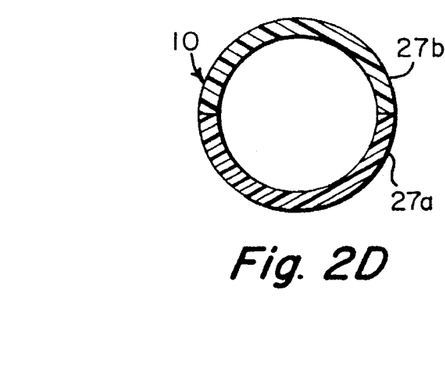
FIG. 2D is a cross section of cutaway shown in FIG. 2C.

As shown in FIGS. 2A and 2B, the esophageal/stomach placement electrode includes a semi-rigid plastic member or tube 10 made of nylon or other suitable material which may be approximately 20 inches long and approximately 3/16 inch in diameter. The tube should be semi-rigid, much like a gastric tube, and be relatively torque free. The distal end 12 of the tube carries an electrode 14, preferably spherical in shape and having a stem 16 that fits within the distal end of the tube. The electrode may be pressed in place or suitably fastened by other type of fasteners. In a preferred form, the electrode 14 is 0.25 inches in diameter, which just exceeds the diameter of the tube 10 so that the electrode will make positive contact with the esophageal or stomach wall when the distal end 12 of the tube 10 is angularly displaced.

The tube 10 has a bendable portion 27 disposed, a distance away from the electrode 14 of the tube 10. The bendable portion facilitates the tube bending at a specific location and orienting the bend in a specific direction. The bendable portion has an interior portion 27a and an exterior portion 27b with respect to the bend. The interior portion 27a is softer and more bendable than the exterior portion. This may be accomplished by cutting away the tubing material and replacing it with material which is softer and more bendable such as PEBAX 3533, which is a brand name of a polyether block polyamide copolymer. FIG. 2B shows an alternative design which effects the same result. In this design, a bendable portion 27 of the tube 10 is corrugated 11 for approximately 180° on circumference of the tube.

A rigidizing member 32, or rigidizer, whose outer diameter is slightly smaller than the inner diameter of the tube 10 is positioned inside the tube at bendable portion 27 and spans the bendable portion 27. When the rigidizing member 32 is positioned at the bendable portion 27 the tube 10 is prevented from bending. Such a feature facilitates entry of the tube 10 into the esophagus and stomach. A control cable 34 is attached to the proximal end 38 of the rigidizing member 32 and extends beyond the proximal end of the tube 10 to the control mechanism 20 (shown in FIG. 1). When the cable 34 is pulled in the proximal direction, the rigidizing member 32 moves axially in the tube 10 toward the proximal end of the tube 10 and away from the bendable portion 27.

As shown in FIG. 2A, a tip wire 64 has one end attached to the electrode 14 at the distal end of the tube 10. A sleeve is crimped to the other end of the wire and is sized to fit within the rigidizing member 32. The distal end 40 of member 32 is spun to a smaller diameter than the remaining portion of member 32. The smaller diameter is large enough to allow the tip wire 64 to pass through, but small enough to capture the crimped sleeve 60 in the member 32.

The sleeve 60 on tip wire 64 is positioned toward the proximal end of the bendable portion 27. As the control cable 34 is pulled in the proximal direction, the member 32 moves axially toward the proximal end of the tube 10 and beyond the bendable portion 27 so as not to interfere with the bending of the tube. As the sleeve moves beyond the bendable portion 27, the distal end 40 of the member 32 engages the crimped sleeve 60. Continued pulling of control cable 34 pulls the member 32 and engages the sleeve 60. This, in turn, pulls the tip wire 64, and effects the bending of the tube 10 at the bendable portion 27.

After use, a return wire 36 is pulled and moves the member 32 axially and in the distal direction to the bendable portion. This straightens tube 10 so that the device may be withdrawn from the esophagus. (The return wire 36 passes through the member 32, through an eyelet 15 on the electrode 14 inside the tube 10 and is attached to the distal end of the member 32. When the return wire 36 is pulled, the member is moved in the distal direction to the bendable portion 27).

Figure 3:
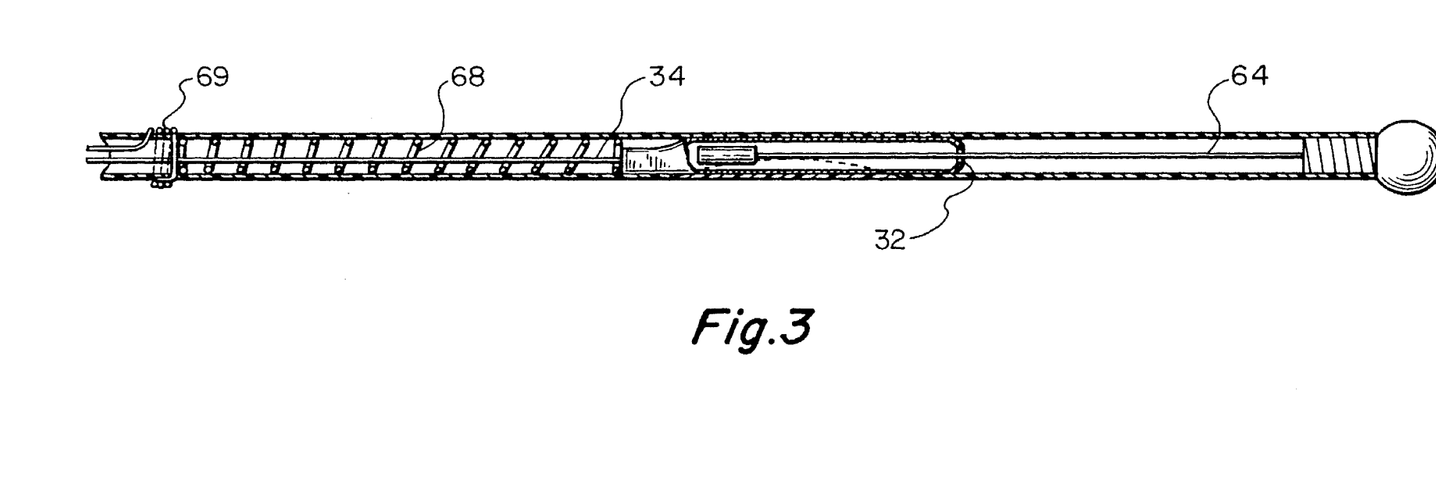
FIG. 3 shows another embodiment of the invention.

FIG. 3 shows another preferred embodiment of the invention. In this embodiment, the actuation of the bending is the same, but the mechanism to straighten the tube is different. Instead of using a return cable, a spring 68 is disposed at the proximal end of the member 32. A spring stop 69 is provided to restrain the axial motion of the spring 68. As the member 32 is pulled in the proximal direction, the spring 68 provides a biasing force urging the member 32 toward the hinged portion 27 such that when the pulling force is released, the member 32 is pushed back to the bendable portion 27.

The electrode typically may be used in the following manner. The tube 10 is inserted into the esophagus either through the mouth or the nasal passage to a depth wherein the electrode 14 and the bendable portion 27 are disposed beyond the lower end of the esophagus into the stomach to permit angular actuation of the distal end 12 of the tube 10 from its straight or insertion configuration as shown in FIG. 4 to the configuration of FIG. 5. The external electrode also forming part of the electrical circuit is mounted on the chest of the patient and the controls (not shown) to operate the electrodes are properly set. In order to reduce the amount of electrical energy required to achieve pacing or other of the functions described in the earlier patents cited in the introduction, the operator moves the control cable 34 to move the member 32 in the axially direction toward the proximal end of the tube and beyond the bendable portion 27. When the member 32 is moved beyond the bendable portion 27 in the proximal direction, the crimped end of the tip wire 64 pulls the distal 12 of the tube 10 causing it to bend at the bendable portion because of the softer material at one side of the tube in an angular position at the bendable portion 27. The angular actuation of the distal end 12 of the tube 10 places the electrode 14 in close proximity to the upper stomach wall near the heart ventricle V, as shown in FIG. 5. Further deflection of the distal end 12 of the tube 10 or pulling the tube 10 in a proximal direction (or a combination of the two) places the electrode 14 in firm contact with the upper stomach wall to enhance the electrical contact of the electrode with the ventricle V of the heart, as shown in FIG. 6. In the position shown in FIG. 6, the electrode 14 is able to operate effectively with the external electrodes placed on the body by minimizing the electrical resistance between the two electrodes. When the procedure is completed, the operator causes the tube to straighten by causing member 32 to move back into the bendable portion 27 of tube 10. Thereafter the tube 10 may be withdrawn from the stomach and esophagus.

From the foregoing description, those skilled in the art will appreciate that the present invention provides a very convenient means for enabling an operator to place an esophageal/stomach placement electrode very close to the heart or other organ by means of a non-invasive procedure and thereby reduce the energy required to carry out the particular procedure such as pacing or defibrillation upon the patient. It will be appreciated that while specific embodiments are shown in the drawings and disclosed in the specification, modifications may be made without departing from this invention. Because modifications may be made to the invention without departing from its spirit, it is not intended that the scope of this invention be limited to the specific embodiments illustrated and described. Rather, the scope of the invention is to be determined by the appended claims and their equivalents.

We claim:

1. An esophageal/stomach placement electrode comprising:

a tube having proximal and distal ends adapted to be inserted into an esophagus, an electrode carried by said tube in the region of the distal end, a bendable portion provided in the tube at the distal end causing the tube to bend in one direction in response to an axial pull in a proximal direction on the distal end of the tube, said bendable portion having one side made of stiffer material than the opposite side thereof, and an actuation mechanism contained within said tube and attached to the distal end of the tube and extending beyond the proximal end of the tube for exerting a pull on the distal end of the tube in the axial direction for causing the tube to bend in the said opposite side of the tube.

2. An esophageal/stomach placement electrode as described in claim 1 further comprising:

a rigidizer which makes rigid said portion of tube and is axially movable within the tube.

3. An esophageal/stomach placement electrode as described in claim 2 wherein the tube has a proximal end and further comprises:

a first wire disposed in the tube having one end attached to the electrode and the other end operatively connected to the rigidizer, a second wire disposed in the tube, said second wire having one end attached to the rigidizer and another end which extends beyond the proximal end of the tube.

4. An esophageal/stomach placement electrode as described in claim 3 wherein the tube includes a distal end and the first and second wires are disposed entirely within the tube at said distal end.

5. An esophageal/stomach placement electrode as described in claim 3 further comprising:

a means for biasing said rigidizer toward the distal end.

6. An esophageal/stomach placement electrode as described in claim 5, wherein:

said means for biasing includes a spring disposed on a proximal side of the rigidizer and a spring stop mounted to the tube and disposed on a proximal side of the spring.

7. An esophageal/stomach placement electrode as described in claim 5, wherein:

said rigidizer is a stiff hollow member whose outer diameter is smaller than the inner diameter of the tube, the end of the first wire which is operatively connected to the rigidizer has a solid sleeve crimped on the end, a distal end of the rigidizer including an opening that is large enough to permit the first wire to slide smoothly therethrough and small enough to capture said sleeve.

8. An esophageal/stomach placement electrode for placing an electrode in a body comprising:

a tube having a proximal end and a distal end adapted to be inserted into an esophagus, an electrode carried by said tube in the region of the distal end, a rigidizing means for rigidizing a portion of said tube which is inside the tube and axially movable therein, means for biasing said rigidizing means toward the distal end of the tube, and an actuating mechanism for angularly displacing the distal end of the tube, said actuating mechanism being disposed entirely within the tube and controlled from a point external from the body for causing the distal end of the tube to angularly displace.

9. An esophageal/stomach placement electrode as described in claim 8, wherein:

said means for biasing includes a spring disposed on a proximal side of the rigidizing means and a spring stop disposed in said tube on a proximal side of the spring.

10. An esophageal/stomach placement electrode as described in claim 9, wherein:

said rigidizing means is a stiff hollow member whose outer diameter is smaller than the inner diameter of the tube, a first wire having an end which is operatively connected to the rigidizing means and has a solid sleeve crimped on said end, said member having a distal end that is open enough to permit the first wire to slide smoothly therethrough and closed enough to prevent said solid sleeve from passing therethrough.

11. A method of noninvasively placing an electrode in the body adjacent to a selected body organ comprising the steps of:

inserting a tube that has an electrode at a distal region through the esophagus, the tube having a hinge portion and a rigidizer;

angularly displacing the distal region of the tube by axially moving the rigidizer beyond the hinge portion of the tube to place the electrode in contact with the stomach wall such that the stomach and electrode are closely adjacent to the selected organ; the rigidizer being operatively connected to the electrode tip such that when the rigidizer has moved beyond the hinge portion continued motion of the rigidizer angularly displaces the electrode.

12. An esophageal/stomach placement electrode for placing an electrode in a body comprising:

a tube having a proximal end and a distal end adapted to be inserted into an esophagus, said tube including a hinge portion that enables the distal end of the tube to be displaced at a predetermined location, an electrode carried by said tube in the region of the distal end, a rigidizing means for rigidizing a portion of said tube which is inside the tube and axially movable therein, an actuating mechanism for angularly displacing the distal end of the tube, said actuating mechanism being disposed entirely within the tube and controlled from a point external from the body for causing the distal end of the tube to angularly displace.

13. An esophageal/stomach placement electrode as described in claim 12 and further comprising:

a means for biasing said means for rigidizing means toward the distal end.

14. An esophageal/stomach placement electrode as described in claim 13 wherein:

said means for biasing includes a spring disposed on a proximal side of the rigidizing means and a spring stop disposed in said tube on a proximal side of the spring.

* * * * *